United States Patent [19]
Waisman

[11] Patent Number: 5,591,188
[45] Date of Patent: Jan. 7, 1997

[54] SURGICAL INSTRUMENT FOR IMPACT INSERTION OF AN INTRAOSSEOUS TROCAR-NEEDLE

[75] Inventor: Marc Waisman, Kiryat Bialik, Israel

[73] Assignee: Wais-Med Lmt, a subsidiary company of Teic Technion Enterpreneurial Incubator Ltd., Nesher, Israel

[21] Appl. No.: 332,860

[22] Filed: Nov. 1, 1994

[30] Foreign Application Priority Data

Apr. 12, 1994 [IL] Israel ........................................ 109294

[51] Int. Cl.⁶ .................................................. A61B 10/00
[52] U.S. Cl. ........................... 606/182; 606/185; 604/157
[58] Field of Search ..................... 606/108, 167, 606/181, 182, 185, 79; 128/749–754; 604/51, 115, 117, 135, 136, 156, 157, 264

[56] References Cited

U.S. PATENT DOCUMENTS

| | | |
|---|---|---|
| 4,316,463 | 2/1982 | Schmitz et al. ................ 604/135 |
| 4,369,870 | 1/1983 | Taylor . | |
| 4,766,907 | 8/1988 | Groot et al. ...................... 128/754 |
| 4,969,870 | 11/1990 | Kramer et al. . | |
| 5,271,744 | 12/1993 | Kramer et al. . | |
| 5,357,974 | 10/1994 | Baldridge ......................... 128/754 |
| 5,368,046 | 11/1994 | Scarfone et al. ................. 604/117 |

*Primary Examiner*—Stephen C. Pellegrino
*Assistant Examiner*—Glenn Dawson
*Attorney, Agent, or Firm*—Frishauf, Holtz, Goodman, Langer & Chick

[57] ABSTRACT

A surgical instrument serves to insert a trocar needle into the bone marrow of a patient for connection of a syringe, an infusion set or the like. The instrument includes a cylindrical housing containing a sliding bolt and the trocar needle configured to be forcefully shot through the bone material into the marrow by release of a compressed helical spring. The bolt holds the rear end of the needle in a releasable grip permitting the needle to be released and to remain in the bone. The helical spring is positioned in the rear of the housing and of the bolt and is held in compressed state by a catch which is releasable by pressure on a trigger. This shoots the bolt and the needle forwards, a collar in the housing stopping the bolt sharply and allowing the needle to be released from the device after its penetration and to be connected to a syringe or an infusion set for intraosseous injection, infusion or other treatment.

14 Claims, 5 Drawing Sheets

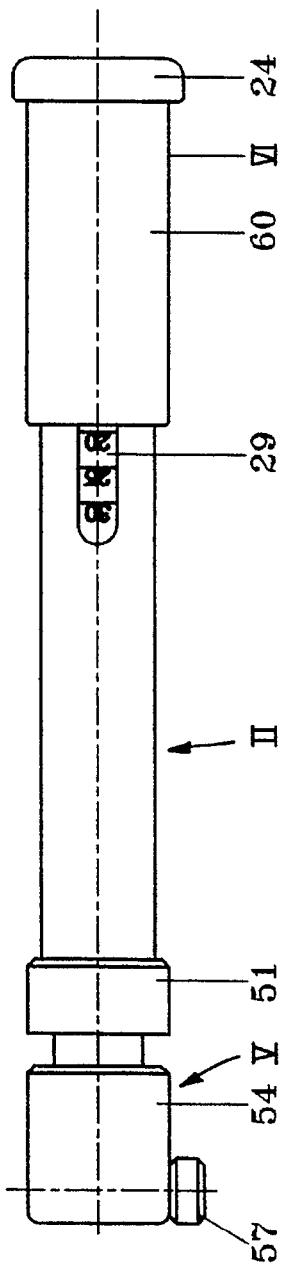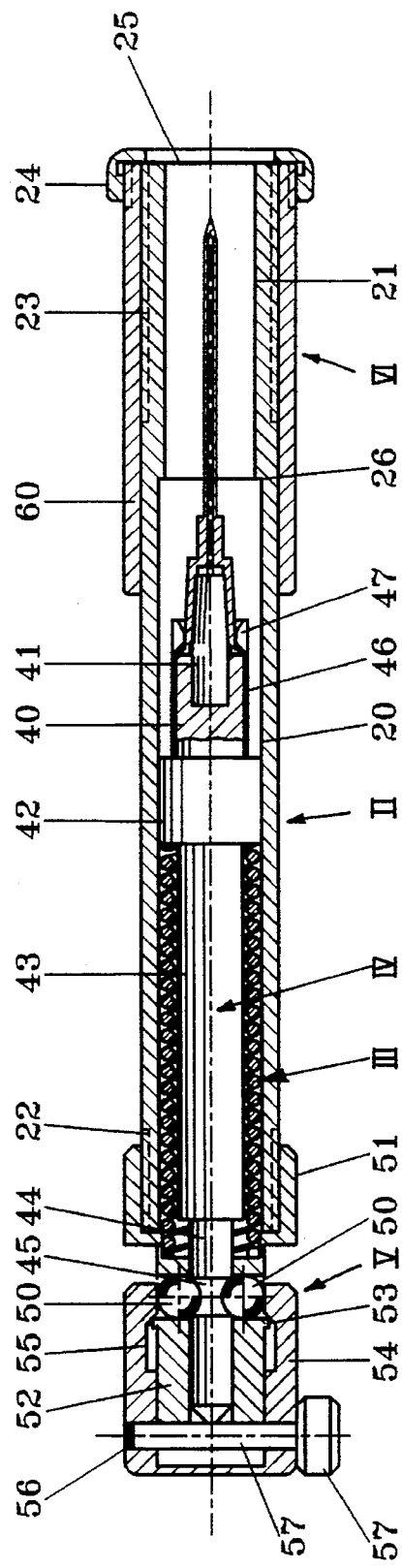
FIG. 3
FIG. 4

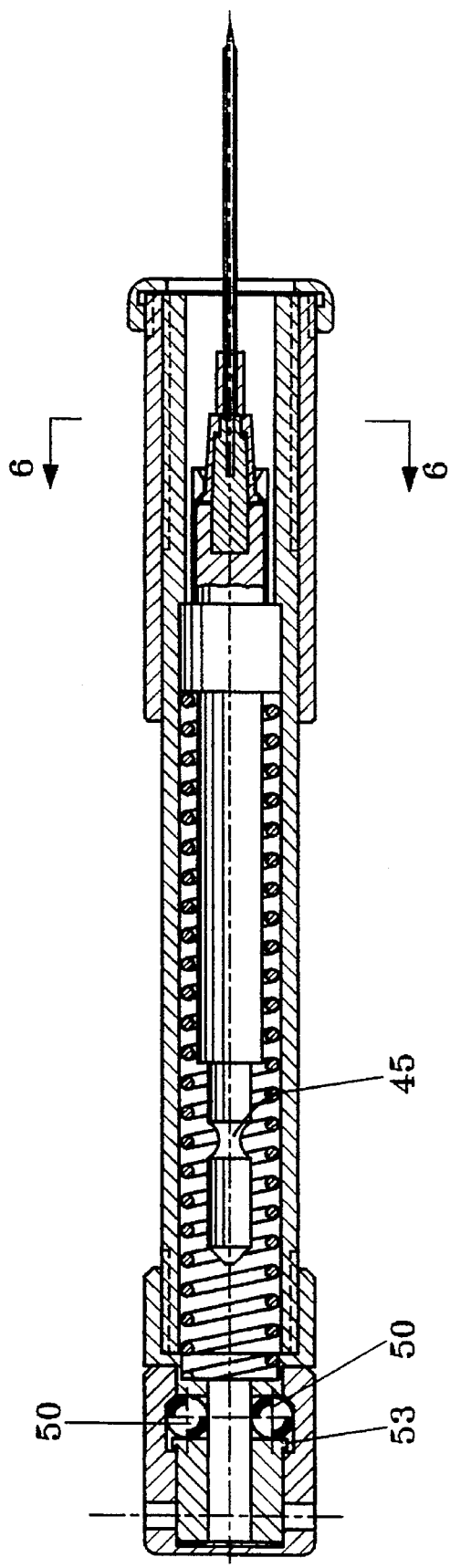
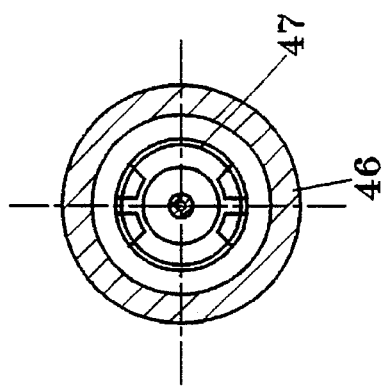
FIG. 5
FIG. 6

SURGICAL INSTRUMENT FOR IMPACT INSERTION OF AN INTRAOSSEOUS TROCAR-NEEDLE

BACKGROUND OF THE INVENTION

The invention relates to a surgical instrument for impact insertion of a trocar-needle into a bone for the purpose of connecting to the needle an infusion or transfusion set or a syringe containing any medicine to be injected for medical treatment of a human or animal patient. It relates particularly to an instrument suitable for instantaneous insertion of a trocar-needle, be it in a battle field, the site of an accident, or any other occasion where instantaneous infusion or itravascular injection becomes necessary. It is especially necessary in the case of newborns or children where it is often difficult to find a vein. But also with adults it often becomes necessary to find an alternative route to intravenous infusion, for rapid vascular access. Likewise for the purpose of marrow aspiration or transplantation.

Intraosseous infusion and bone marrow transfusion was first introduced in the forties of this century, and was especially used in emergency cases during World War II, to avoid the lengthy times needed for finding the suitable blood vessel for insertion of the needle. Nowadays the method is well known, but not much in use, because of the difficulty to forcefully drive a needle or a trocar into the bone with resulting great pain, on the one hand, and the danger of infection owing to the necessity to provide an opening through the skin and the tissue surrounding the bone. The conventional trocar used is in the form of a sharp stylet enclosed in a tube (cannula) and inserted through the containing wall of the bone, whereafter the stylet is withdrawn permitting fluid to be infused or to be drained through the tube.

Infusion, injection of drugs, resuscitation and anesthesis through a major vein or peripheral vein often cause complications which can easily be avoided by intraosseous infusion. There exist a few medical instruments for intraosseous infusion injection or aspiration, but they differ considerably from the present device which is characterized by the operation of forcefully driving a trocar needle into the bone, releasing it from the device and leaving it in the bone for subsequent attachment of the needle to a syringe, an infusion or transfusion set.

The following patents are cited as prior art, but they differ from the present device in their essential functions:

U.S. Pat. No. 4,969,870 (Kramer et al.) describes a tube having an upper end for connection of an infusion set and an enlarged lower end which is rotatably advanced through the cortical bone into the trabecular bone.

U.S. Pat. No. 5,271,744 (Kramer et al.) discloses a device for rapid vascular drug delivery, including a syringe body fitted with a needle. A compressed helical spring is released to drive a plunger into the syringe body and simultaneously driving the needle into the bone and injecting the drug. A second helical spring serves to extract the needle immediately after the medication has been injected.

It is the main object of the present invention to provide a specially designed trocar-needle and an instrument which will drive it into the bone while causing almost no pain to the patient due to high velocity penetration of the trocar-needle, and to leave it in situ for infusion, transfusion aspiration, and other medical treatment.

It is another object of the present invention to provide an instrument which will automatically insert the needle into the bone to a predesignated depth.

Still another object is to provide an instrument for the above purpose which is practically foolproof and easily handled by any surgeon, nurse, medic or paramedic in the battlefield, as well as in ambulances, air transport and especially in the emergency room of a hospital or a ward, and in any occasion as an alternative to intravenous injection, infusion or other medical treatment.

Still another object is to provide a surgical instrument which can be readily sterilized for re-use, but the main idea is to produce it at low cost so as to permit its disposal after a single use.

SUMMARY OF THE INVENTION

The surgical instrument or "gun" serving to insert a trocar-needle into a bone of a patient works on the known principle that a compressed or "cocked" spring is released from its cocked position, after a safety catch has been opened, thereby driving the trocar-needle in the forward direction at high velocity in order to avoid pain to the patient. However, the present instrument differs from the conventional injection instruments in that it releases the needle after its penetration into the bone and permits its connection to a syringe or an infusion or transfusion set.

This operation requires a needle strong and sturdy enough to be driven into the hard bone without being bent or broken and to be shaped in a form to prevent bone or tissue material from clogging the front opening. This requirement has resulted In the design of the present trocar-needle which has the external shape of a conventional hypodermic needle, whereof the front end is in the form of a sharp point closing the lumen of the tube in the needle, while forming communication between the lumen and the outside by one or more transverse holes in the tube wall close to the front end.

The surgical instrument of the invention includes a housing containing the afore mentioned trocar needle in its front portion and a compressed helical spring in its rear portion, as well as a trigger mechanism and safety catch at its rear end. The housing is in the form of a hollow cylinder having its rear end closed by a cap and its front end by a penetrable diaphragm to prevent impurities from entering the housing. The diaphragm also serves to prevent the needle from being shot out of the instrument in case of its accidental operation, by retaining the thicker rear portion of the needle. The housing encloses a long bolt which holds at its front end a resilient member for releasably holding the rear end of the trocar needle and has its rear end retained in cocked position by trigger means. The front portion of the bolt is of a diameter coextensive with the smooth bore of the housing permitting its smooth motion in the forward direction, while its rear portion is of a much smaller diameter and is surrounded by the helical spring which is held in compressed state between the front portion of the bolt and the rear cap.

In a preferred embodiment a screw-threaded sleeve is mounted on the front of the housing, which is rotatably movable in the axial direction and configured to define the depth to which the needle is to penetrate into the bone.

The invention includes two different safety catch and trigger arrangements, both designed to hold the spring in compressed state while preventing unauthorized or accidental release. In a first embodiment at least one radial bore is drilled into the rear portion of the housing which contains a steel ball of coextensive diameter. In the cocked state the steel ball holds the bolt in the rearward position by engaging with a circumferential groove in the rear portion of the bolt, while the front end of the rear cap holds the ball inside the groove. The cap, in its part, is held in position by a transverse pin extending through the cap and the housing and serving as a safety catch. The cap has an internal circumferential groove of a depth alike or greater than the depth of the groove in the bolt end. In order to propel the needle, the instrument is placed onto the skin covering the bone portion to be penetrated, the safety pin is pulled out and the cap is pushed in forward direction. This causes the at least one ball to slip out of the groove in the bolt into the groove of the cap, whereby the bolt is released and shot forward by the expanding spring. A stop on the inside of the housing stops the bolt, after the needle has penetrated into the bone to the desired depth, and by pulling the instrument to the rear the resilient member releases the end of the needle which is now free to receive the connector of an infusion set or a syringe.

Another embodiment of the trigger and safety catch includes a screw cap covering the rear end of the housing and holding a trigger handle. The rear end of the bolt is positioned in a central bore of the cap and is held in cocked position by a transversely movable pin engaging a groove in the bolt. This pin is, in its part, held in bolt-engaging position by a second pin at right angles to it which engages a recess in the first pin. A trigger handle is in contact with the sideways-protruding end of the first pin, but is prevented from pushing it inwards by the safety catch pin. By pulling out the safety catch the first pin becomes axially movable and can be pressed into the cap by movement of the trigger handle, thereby moving it out of engagement with the groove in the bolt which is thus moved into the recess of the pin and freed out of engagement with the latter. The bolt is shot forward by the expanding spring and the operation becomes identical with the operation described with reference to the first embodiment.

BRIEF DESCRIPTION OF THE DRAWINGS

FIG. 3 is a side view of a first embodiment of the instrument, FIG. 4 is a longitudinal section of the instrument of FIG. 3 in "cocked" position, FIG. 5 is a longitudinal section of the instrument of FIG. 3 in "shooting" state, FIG. 6 is a section along line 6—6 of FIG. 5.

DETAILED DESCRIPTION OF THE DRAWINGS

Figure 1:
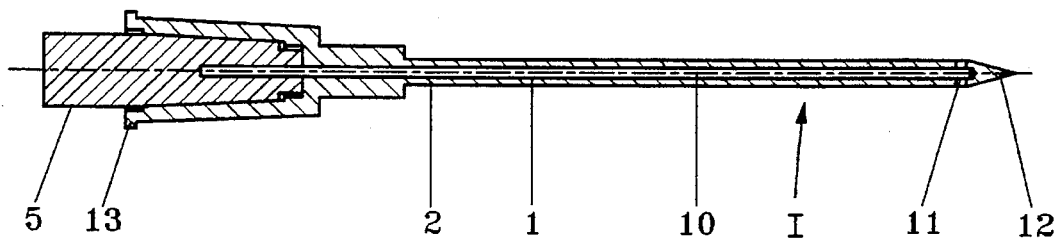
FIG. 1 is a longitudinal section of the trocar needle of the invention.

In the following description the terms "front" or "forward" will be used to define the direction of driving the needle into the bone, while the expression "rear" defines the end of the instrument containing the triggering device.

The instrument or "gun" for driving or shooting a trocar-needle into a patient's bone for injection, infusion, transfusion, aspiration or other treatment includes generally a housing, a helical spring, a bolt, spring-cocking and triggering means, and a device defining the depth to which the trocar is to be driven into the bone.

The trocar-needle I has the external shape of a conventional hypodermic needle with the difference that the lumen 10 stops short of the front end and communicates with the outside—in the present case the inside of the bone—through two transverse bores 11, while the front end is closed in the form of a sharp point 12. The rear end is in the form of a rim 13 for connection to a syringe or an infusion set in the conventional manner. The rear end of the needle encloses a cylindrical block 5 which serves as a reinforcement and is to be removed from the needle after its penetration into the bone.

Figure 2:
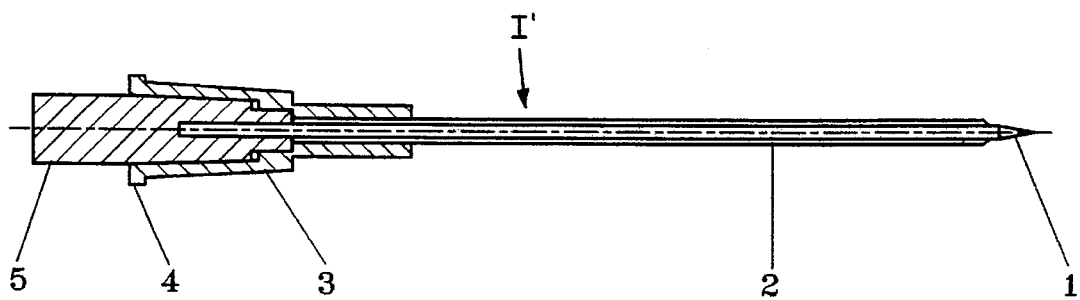
FIG. 2 is a longitudinal section of a conventional trocar needle, likewise used with the present surgical instrument.
Figure 7:
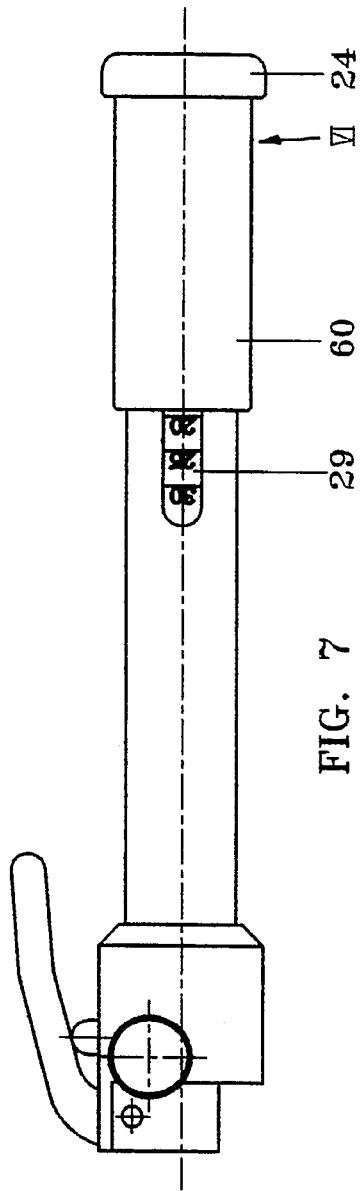
FIG. 7 is a side view of a second embodiment of the instrument.

The conventional trocar needle I' illustrated in FIG. 2 comprises a solid stylet 1 enclosed in a cannula 2 which includes a hollow, frusto-conical rear end 3 terminating in a connecting flange 4. The rear end of the stylet is firmly embedded in a cylindrical block 5 which, after insertion of the trocar-needle is withdrawn from the cannula together with the stylet.

The embodiment of the surgical instrument illustrated in FIGS. 3 through 11 essentially includes a cylindrical housing II, a helical spring III, a bolt IV, a safety catch and bolt-triggering means V, and a device VI configured to limit the depth to which the trocar I or I' is to be driven into the bone.

The embodiment of the Instrument shown in FIGS. 3, 4, 5 and 6 includes a cylindrical housing II which has a smooth bore 20 extending from the rear end to close to the front end which is bored to a somewhat smaller diameter 21, thereby forming a step 26. The rear end is provided with an external screw-thread 22 for attachment of the trigger mechanism and the front end with external screw-thread 23 permitting the lengthwise adjustment of a sleeve 60 on the housing. This sleeve serves to limit the depth to which the trocar enters the bone by extending beyond the front of the housing by a predetermined length effected by rotation of the sleeve on the screw-threaded end of the housing. A centrally perforated cap 24 is screwed onto the front of the sleeve and presses a diaphragm 25 onto the sleeve's front end.

The bolt IV comprises a front end 40 which is centrally bored (41) for holding the cylindrical block 5 of the trocar needle I' (FIG. 2). The front end is covered by an elastic sleeve 46 forming at its front end several inwardly extending fingers 47 (FIG. 6) which releasably grip the flange of either the trocar needle of FIG. 1 or of the cannula 2 shown in FIG. 2. Beyond the front end the bolt forms a piston 42 which is slidingly movable in bore 20 of the housing, while the main cylindrical portion 43 is surrounded by spring III. The rear end 44 is of smaller diameter than that of the main portion and contains a circumferential groove 45 holding, in cocked state, two steel balls 50.

At this opportunity it should be mentioned that the needle in FIG. 4 is a trocar-needle as illustrated in FIG. 1, while FIG. 5 shows the conventional trocar-needle illustrated in FIG. 2.

The rear end of the housing is closed by a screw cap 51 which is elongated towards the rear in the form of a centrally perforated cylinder 52. The latter is additionally perforated by a bore 53 perpendicular to its axis, permitting axial motion of the two steel balls 50. These balls are held in position inside groove 45 by a sliding cap 54 slidingly movable on cylinder 52 and provided with an internal circumferential groove 55. The sliding cap is held in safe position by a safety pin 57 mounted in a crosswise extending bore 56 at the end of the cap.

The instrument is operated as follows: In the cocked state (FIG. 4) spring III is held in compressed state between piston 42 and screw-cap 51 owing to the fact that the steel balls hold the bolt in a rearward position by engagement with groove 45. For the purpose of driving the needle into the bone, safety pin 57 is pulled out, the front of the instrument is placed onto the skin covering the bone to be pierced and sliding cap 54 is pushed forwards. This movement allows the steel balls to leave groove 45 in the bolt and to enter groove 55 in the cap whereby the bolt is free to be moved forwardly by the force of the expanding spring and to insert the needle into the bone, after having pierced membrane 25. The forward motion of the bolt is abruptly stopped by step 26 at the end of the rear bore of the housing, whereby fingers 47 release the flange of the trocar-needle or of the cannula which now remains inside the bone, while the instrument is removed. An infusion set or other medication set is now connected to the the end of the trocar needle or the cannula for the purpose of medication. Previous to operating the instrument, the depth to which the needle should enter the bone may be determined by unscrewing sleeve 60 from the housing until it extends beyond the housing front by a length, as indicated by a scale 29 on the outside of the housing. (FIG. 3).

The second embodiment of the surgical instrument illustrated in FIGS. 7 through 11 differs from the afore described instrument only in the arrangement of the safety catch and the trigger mechanism, and for this reason only those parts will be described in the following, while the other components are identical with those of the first embodiment and need not be described again.

Figure 8:
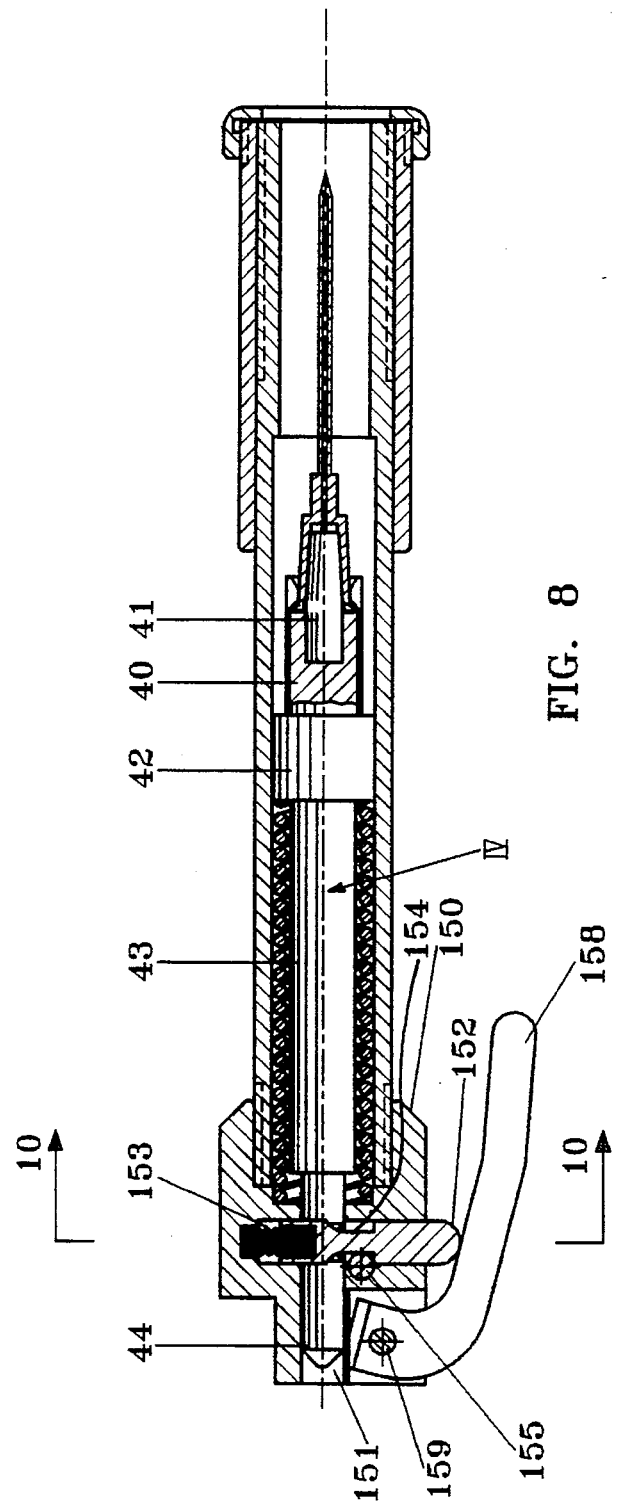
FIG. 8 is a longitudinal section of the instrument shown in FIG. 7, in "cocked" position.
Figure 10:
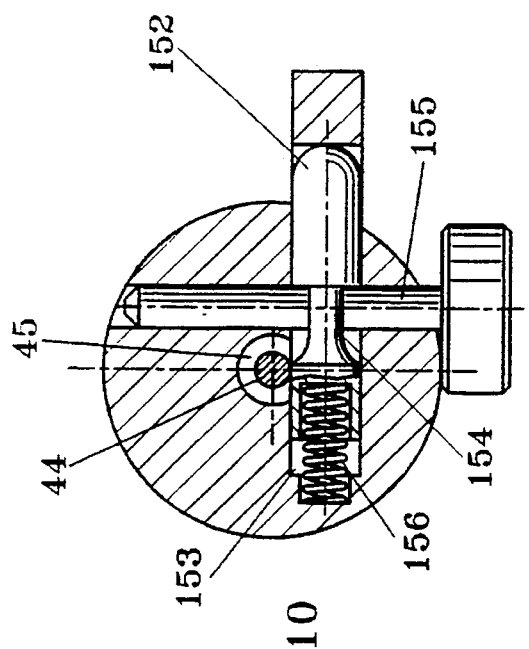
FIG. 10 is a section of the instrument of FIG. 8 along line 10—10, and, FIG. 11 is a section of the instrument of FIG. 9 along line 11—11.

Referring now to FIGS. 8 and 10 showing the instrument in the cocked state: The rear end of housing II is closed by a cap 150 which is centrally perforated for containing in the bore 151 thereof, the rear portion 44 of the bolt. The bolt is provided with a circumferential groove 45 similar to that shown in the first embodiment which is in engagement with a cross bolt 152 axially movable in a bore 153 in the cap. The cross bolt is provided with a circumferential groove (154) which is engaged by a safety pin 155 preventing it from slipping out of engagement with bolt IV. The cross bolt is urged in an outward direction by a helical spring 156 mounted at the end of bore 153. A trigger 158 is hingedly attached by a pin 159 attached in a slot of cap 150.

Figure 9:
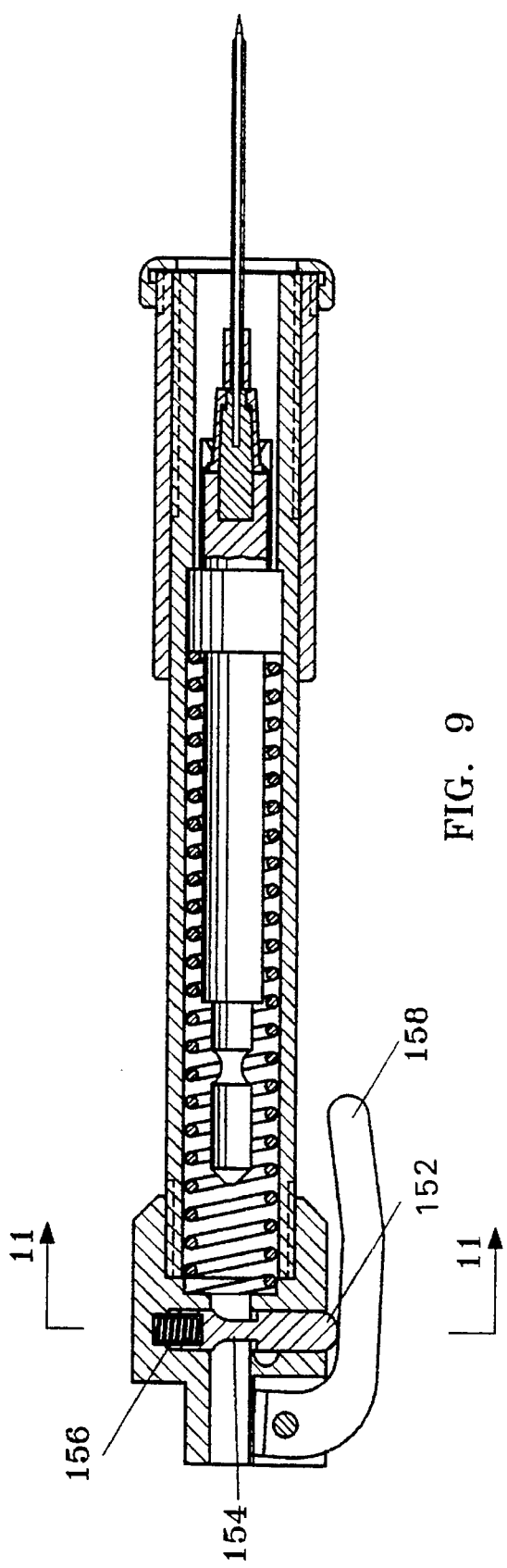
FIG. 9 is a longitudinal section of the instrument of FIG. 7 in "shooting" state.
Figure 11:
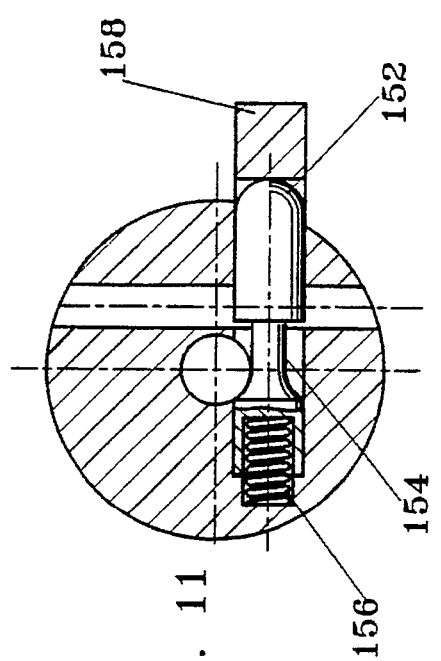

Looking now at FIGS. 9 and 11 showing the position of the bolt after removal of the safety pin and pressure on the trigger 158 moving cross bolt 152 inwardly. The cross bolt has been free to be moved against the force of spring 156, by removal of safety pin 155 out of groove 154 which latter now permits bolt IV to be shot forward, since the groove permits its free motion.

The operation of this instrument is similar to that described in respect of the first embodiment: the depth of penetration is adjusted by means of sleeve 60, the safety pin is pulled out and the instrument is placed in position, whereupon the trigger is pulled. The needle or the cannula respectively are released from the instrument and are connected to an infusion set or a syringe.

Finally it should be noted that the two embodiments of the triggering mechanism constitute only examples of the many means of releasing the bolt, and that they may be altered and modified by a person skilled in the art, within the scope of the appended claims.

I claim:

1. A surgical instrument for forcefully driving a trocar needle into a patient's bone through the skin and the tissue by the force of an expanding helical spring, and for releasing said trocar needle for connection of a syringe, an infusion or medication set to said trocar needle, the instrument including:

a longitudinal housing having a front end and a rear end, said housing being in the shape of a hollow cylinder including a smooth bore extending from its rear end to a stop close to its front end, a screw cap closing the rear end of said housing, said screw cap having a rear portion extending beyond the rear end of said housing, a trocar needle having a sharp front end for penetrating said bone and a rear end surrounded by an outstanding connecting flange, said needle being positioned, in a cocked state, in said housing with its sharp front end close to the front end of said housing, a bolt slidingly positioned in said housing, having a first front portion provided with means for releasably holding the rear end of said trocar needle, a second portion of a diameter coextensive with said smooth bore in said housing positioned to the rear of said stop, a third portion of smaller diameter, and a rear portion provided with means for being held in said rear portion of said screw cap in the cocked state, safety catch means positioned in said screw cap for engagement with said means for being held to releasably hold said rear portion of said bolt, a helical spring surrounding said third portion of said bolt and being held in a compressed state between said second portion of said bolt and said rear portion of said screw cap, whereby said bolt is shot in a forward direction by the force of said helical spring as it expands when said safety catch means releases said rear portion of said bolt, and is stopped by contact of said second portion with said stop in said housing, effecting release of said trocar needle from the front portion of said bolt.

2. The instrument of claim 1, wherein said trocar needle has a lumen extending from its rear end to close to its front end which is closed in the shape of a sharp point, and at least one transverse hole close to said sharp point in communication with said lumen communication between said lumen and an outside being effected by at least one transverse hole close to said sharp point.

3. The instrument of claim 1, wherein said trocar needle includes:

a sharp inner stylet rigidly connected to the front portion of said bolt by means of a cylindrical block at a rear end of said stylet, said stylet including said sharp front end, and a cannula adapted to be left in the bone after insertion, said cannula enclosing said stylet and including said rear end, wherein said block and said stylet remain attached to said bolt and are withdrawn together with said surgical instrument.

4. The instrument of claim 1, wherein said means for releasably holding said trocar needle is in the form of a sleeve mounted on said front portion of said bolt and provided with elastic inwardly directed fingers configured to grip said connecting flange on said trocar needle.

5. The instrument of claim 1, wherein said bolt comprises a circumferential groove in said rear portion serving for engagement with said safety catch means.

6. The instrument of claim 5, wherein:

said screw cap includes a transverse bore, said safety catch means comprises at least one steel ball movable in the transverse bore in said screw cap, and further comprising:

a second cap which urges said at least one steel ball into said groove in said bolt, said second cap slidingly movable on said screw cap, and a transverse pin which releasably holds said second cap in a "safe" state, preventing forward sliding movement of said second cap on said screw cap.

7. The instrument of claim 6, wherein said sliding cap is provided with an internal circumferential groove positioned to the rear of said at least one steel ball, while said sliding cap is in a rearward position, permitting said at least one steel ball to enter said circumferential groove of said sliding cap and to leave said groove on said bolt, so as to release said bolt to be shot forward by said expanding spring after withdrawal of said transverse pin and a forward push of said sliding cap.

8. The instrument of claim 5, wherein:

said screw cap includes a transverse bore, said safety catch means comprises a first pin movable in said transverse bore in said screw cap, said pin having a straight portion and a circumferential groove, whereby the straight portion of said first pin engages said circumferential groove in said bolt to hold said bolt in a "safe" state and disengages said bolt by axial movement of said pin into coinciding position of said two grooves, permitting said bolt to be driven in the forward direction by said expanding spring.

9. The instrument of claim 8, wherein said first pin is held in a "safe" state by a second pin movable in a second transverse bore in said screw cap and engaging said groove in said first pin.

10. The instrument of claim 8, wherein:

said transverse bore has an open end and a closed end, said first pin protrudes out of said open end, and a helical spring is positioned in said bore at said closed end.

11. The instrument of claim 10, further comprising trigger means for axially moving said first pin from the "safe" state into a "shooting" state, said trigger means pivotally fastened to said screw cap and configured to move said first pin against the force of said helical spring positioned in said bore at said closed end.

12. The instrument of claim 1, wherein the front end of said housing is provided with external screw threads, and wherein a sleeve having a front end and a rear end and corresponding internal screw threads is movable along said housing by rotational motion to a position in which the front end of said sleeve extends beyond the front end of said housing by a distance defining the depth to which said trocar needle will enter the bone.

13. The instrument of claim 12, wherein a numerical scale is provided on the outside of said housing, indicating the depth of entry of said trocar needle by a number appearing at the rear end of said sleeve.

14. The surgical instrument of claim 1, further comprising trigger means coupled to said safety catch means for releasing said safety catch means.

* * * * *